(12) United States Patent
Berg-Schultz et al.

(10) Patent No.: US 7,388,102 B2
(45) Date of Patent: Jun. 17, 2008

(54) ORGANOSILICONE DERIVATIVES OF AMINO HYDROXYBENZOPHENONES AND THEIR USE AS UV-A FILTERS IN COSMETIC PREPARATIONS

(75) Inventors: Katja Berg-Schultz, Kaiseraugst (CH); Ulrich Huber, Erlenbach (CH)

(73) Assignee: DSM IP Assets B.V., TE Heerlen (NL)

( * ) Notice: Subject to any disclaimer, the term of this patent is extended or adjusted under 35 U.S.C. 154(b) by 300 days.

(21) Appl. No.: 10/511,020

(22) PCT Filed: Mar. 25, 2003

(86) PCT No.: PCT/EP03/03095

§ 371 (c)(1),
(2), (4) Date: May 9, 2005

(87) PCT Pub. No.: WO03/086340

PCT Pub. Date: Oct. 23, 2003

(65) Prior Publication Data

US 2005/0255066 A1    Nov. 17, 2005

(30) Foreign Application Priority Data

Apr. 12, 2002   (EP)   .................................. 02008419

(51) Int. Cl.
*A61K 8/00* (2006.01)
*C07F 7/04* (2006.01)
(52) U.S. Cl. ...................................... 556/436; 556/437
(58) Field of Classification Search ..................... None
See application file for complete search history.

(56) References Cited

U.S. PATENT DOCUMENTS

| | | | |
|---|---|---|---|
| 5,270,426 | A | 12/1993 | Sakuta et al. |
| 6,071,502 | A | 6/2000 | Forestier et al. |
| 6,114,561 | A | 9/2000 | O'Lenick, Jr. |
| 6,409,995 | B1 | 6/2002 | Habeck et al. |
| 2002/0001570 | A1 | 1/2002 | Heidenfelder et al. |

FOREIGN PATENT DOCUMENTS

| | | |
|---|---|---|
| EP | 0 478 284 | 4/1992 |
| EP | 0 655 453 | 5/1995 |
| EP | 0 712 855 | 5/1996 |
| EP | 0 982 310 | 3/2000 |
| EP | 1 046 391 | 10/2000 |
| EP | 1 133 980 | 9/2001 |
| FR | 2 684 551 | 6/1993 |
| GB | 1167759 | 10/1969 |
| WO | WO 01/72935 | 10/2001 |

OTHER PUBLICATIONS

Derwent English language abstract of WO 01/72935.
Derwent English language abstract of EP 0 712 855.
Derwent English language abstract of FR 2 684 551.

*Primary Examiner*—Samuel A Barts
(74) *Attorney, Agent, or Firm*—Bryan Cave LLP

(57) ABSTRACT

The present invention relates to organosilicone derivatives of amino hydroxybenzophenones, a process for their preparation thereof, a cosmetic compositions comprising the organosilicone derivative and the use thereof for protecting hair and/or skin from damage caused by UV-A irradiation.

6 Claims, No Drawings

ORGANOSILICONE DERIVATIVES OF AMINO HYDROXYBENZOPHENONES AND THEIR USE AS UV-A FILTERS IN COSMETIC PREPARATIONS This application is the National Stage of International Application No. PCT/EP03/03095, filed Mar. 25, 2003.

The present invention relates to organosilicone derivatives of amino hydroxybenzophenones, to a process for their preparation, compositions comprising these derivatives and the use thereof.

More particularly, the invention relates to organosilicone compounds comprising a unit of formula I

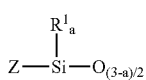
(I)

wherein
a is 0, 1 or 2,
$R^1$ is hydrogen, a saturated or unsaturated $C_1$-$C_{30}$hydrocarbon group or a trimethylsilyloxy group; and
Z is an amino substituted hydroxybenzophenone of formula III

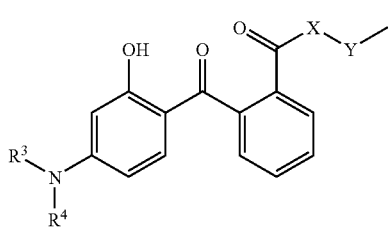
(III)

wherein
$R^3$ and $R^4$ independently are hydrogen, $C_1$-$C_{20}$alkyl, $C_2$-$C_{20}$alkenyl, $C_3$-$C_{10}$cycloalkyl or $C_3$-$C_{10}$cycloalkenyl or $R^3$ and $R^4$, together with the nitrogen atom they are bound to, form a 5 to 6 membered ring;
X is —O— or —$NR^5$— wherein $R^5$ is hydrogen, $C_1$-$C_{20}$alkyl, $C_2$-$C_{20}$alkenyl, $C_3$-$C_{10}$cycloalkyl or $C_3$-$C_{10}$cycloalkenyl; and
Y is a divalent $C_3$-$C_{12}$alkylene or alkenylene chain;
and, optionally, a unit of formula II

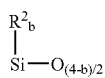
(II)

wherein
b is 0, 1, 2, 3; and
$R^2$ is hydrogen, a saturated or unsaturated $C_1$-$C_{30}$hydrocarbon group or a trimethylsilyloxy group.

Suitable organosilicone compounds are polymeric materials which maybe homopolymers consisting only of such units of formula I, or they may be copolymers containing both units having either the general formula I or II. The units of formula I may be distributed randomly in an organosiloxane polymer, they may be the end blocking units of the polymer or they may be located at the end of the polymer and pending in a chain of the polymer at the same time. The organosilicone compounds may vary from freely flowing liquids to highly viscous gum-like materials or resinous solids.

If a is 2 the two substitutents $R^1$ may be identical or different. If b is 2 or 3 the two or three substituents $R^2$ may be identical or different. If the polymer contains more than one unit of formula I the substituents $R^1$ may be identical or different from unit to unit. If the polymer contains more than one unit of formula II the substituents $R^2$ maybe identical or different from unit to unit.

Examples for a saturated or unsaturated $C_1$-$C_{30}$hydrocarbon group include $C_1$-$C_{30}$alkyl such as methyl, ethyl, propyl and butyl; $C_2$-$C_{30}$alkenyl such as vinyl and allyl; and unsubstituted or substituted aryl such as phenyl, alkaryl and alkoxyphenyl. The hydrocarbon group is unsubstituted or substituted by, e.g. halogen, e.g. a halogenated $C_1$-$C_{18}$hydrocarbon group.

Alkyl and alkenyl may be straight chain or branched, e.g. methyl, ethyl, 3-propyl, 2-propyl, 2-methyl-3-propyl, 3-butyl, 4-butyl, 4-pentyl, 5-pentyl, 6-hexyl, 2-propen-2-yl, 2-propen-3-yl, 3-buten-3-yl, 3-buten-4-yl, 4-penten-4-yl, 4-penten-5-yl, (3-methyl)-penta-2,4-dien-4 or 5-yl, 11-dodecen-11-yl.

Examples for cycloalkyl and cycloalkenyl include cyclopropyl, 2-methyl-cyclopropyl, cyclobutyl, cyclopentyl, cyclohexyl, cyclopropenyl, cyclobutenyl, cyclopentenyl, (3-methyl)-cyclopenta-2,4-dienyl and 11-cyclododecenyl.

The terms "divalent $C_3$-$C_{12}$alkylene chain" and "divalent $C_3$-$C_{12}$alkenylene chain" mean linker groups, in particular linker groups which link the UV absorbing chromophoric residue to the silane, oligosiloxane or polysiloxane moiety. Examples for $C_3$-$C_{12}$alkylene include straight chain or branched saturated hydrocarbon residues such as 3-propylene, 2-propylene, 2-methyl-3-propylene, 3-butylene, 4-butylene, 4-pentylene, 5-pentylene, 6-hexylene, and the like. Examples for $C_3$-$C_{12}$alkenylene include unsaturated hydrocarbon residues containing at least one double bond, such as for example, 2-propen-2-ylene, 2-propen-3-ylene, 3-buten-3-ylene, 3-buten-4-ylene, 4-penten-4-ylene, 4-penten-5-ylene, (3-methyl)-penta-2,4-dien-4 or 5-ylene, 11-dodecen-11-ylene, and the like. The divalent alkylene or alkenylene chains may be interrupted by one or several oxygen atoms. Examples of oxygen interrupted linker groups are e.g. 2-ethyloxy-eth-2-ylene, 4-butyloxy-eth-2-ylene or 3,6-dioxa-8-octylen. Particularly preferred linkers are —CH═CH—$(CH_2)_n$—, —C($CH_2$)—$(CH_2)_n$—, —$CH_2$—$CH_2$—$(CH_2)_n$— and —CH($CH_3$)—$(CH_2)_n$— wherein n is an integer from 0 to 10.

In the organosilicone compounds of the invention the following preferences apply independently, collectively or in any combination or sub-combination:

(a) organosilicone compounds wherein the number of units of formula I is limited to a maximum of 50%, more preferably of 10 to 40%, most preferably 30 to 40% of the total number of siloxane units in the molecule;

(b) liquid substantially linear organosiloxane homopolymers and copolymers, for example those having a viscosity from 50-20000 m$^2$/s;

(c) organosilicone compounds wherein in the units of formula I the following significances apply independently, collectively or in any combination or sub-combination:
(c1) a is 1;
(c2) $R^1$ is methyl in 80%, preferably 100% of units of formula I;

(c3) Y is 2-propylene, 3-propylene, 2-propen-2-ylene, 2-propen-3-ylene, 4-butylene or 3-buten-4-ylene, preferably 2-propen-2-ylene or 2-propen-3-ylene;
(c4) X is —O—;
(c5) $R^3$ and $R^4$ are ethyl;
(d) organosilicone compounds wherein in the units of formula II the following significances apply independently, collectively or in any combination or sub-combination:
(d1) preferably at least two units of formula II are present;
(d2) b is 2;
(d3) $R^2$ is methyl in 80%, preferably 100% of units of formula II.

When a=1 and b=2 the organosilicone compound is a substantially linear or cyclic diorgano-siloxane polymer. However, if the diorganosiloxane is a substantially linear polymer at least two endblocking units must be present, thus requiring either the presence of two units in which a has a value of 2 or two units in which b is 3.

A preferred linear diorgano-siloxane polymer (hereinafter: COMPOUND) is a polymer comprising one structural unit of formula IVa and one structural unit of formula IVb

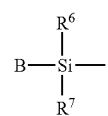

(IVa)

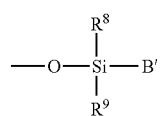

(IVb)

s units of formula IVc

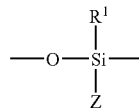

(IVc)

and r units of formula IVd

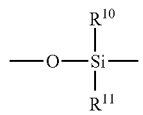

(IVd)

wherein
Z is as defined above;
$R^1, R^6, R^7, R^8, R^9, R^{10}$ and $R^{11}$ independently are as defined above for $R^2$;
B and B' independently are a group Z or a group $R^2$;
r is an integer from 0 to 200; and
s is an integer from 0 to 50, wherein at least B or B' is Z when s is 0.

The compounds of the invention may be prepared by hydrosilylation of an organosilicone compound in which each unit of formula I is replaced by a unit having the formula VI (hereinafter: SiH derivatives).

(VI)

SiH derivatives are well known in the silicone industry and are commercially available. They are described, for example, in the following patents: U.S. Pat. Nos. 3,220,972, 3,697,474 and 4,340,709.

The hydrosilylation may be carried out by reacting the SiH derivative in the presence of a transition metal catalyst, e.g. platinum on charcoal or a platinum complex catalyst, such as e.g. divinyl-tetramethyl disiloxane platinum complex with a compound of formula VII

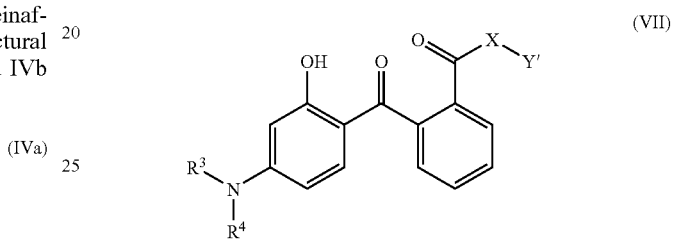

(VII)

in which $R^3$, $R^4$ and X are as defined for formula III and Y' has the same definition as Y in formula III, but is terminated either with a double or a triple bond. The addition may proceed at both positions of the unsaturated carbon-carbon bond, leading to isomeric mixtures of organosilicone products e.g. containing exo and endo double bonds.

The hydrosilylation may be performed in a suitable reaction solvent, e.g. in isopropanol or toluene. The reactants may be present in about equal molar amounts. The reaction may be run at an elevated temperature, e.g. in a range of from 40° C. to 150° C., preferably from 60° C. to 100° C., e.g., at about 80° C.

Compounds of formula VII are generally known and may be prepared, e.g., according to the procedure described in EP 1,046,391 by acylation of the corresponding amino substituted phenols followed by reaction with the respective alcohol or amine such as propinol, allyl alcohol, vinyl alcohol, prop-2-ynyl amine or vinyl amine. Exemplary amino hydroxybenzophenones which are particulary suited for the preparation of the compounds of the invention include 2-(4-diethylamino-2-hydroxybenzoyl)benzoic acid prop-2-ynyl ester, 2-(4-diethylamino-2-hydroxybenzoyl)benzoic acid allyl ester, 2-(4-diethylamino-2-hydroxybenzoyl)benzoic acid vinyl ester and 2-(4-diethylamino-2-hydroxybenzoyl)benzoic acid N-prop-2-ynyl benzamide.

The compounds of the present invention have adsorption maxima in the UV-A region and are effective in absorbing ultra violet radiation in the UV-A range (320-400 nm) which makes them particularly suitable for use in cosmetic sunscreen preparations where absorption in the UV-A range is particularly desirable.

Thus, the present invention also relates to compositions comprising the novel organosilicone compounds, formulated into a suitable support or substrate. Typically, the compositions of the invention are adopted for protecting a material that is sensitive to ultraviolet radiation, in particular solar radiation, such as skin and/or hair and comprises an effective photoprotective amount of an organosilicone compound of the invention.

For the preparation of light screening agents, especially of preparations for dermatological and/or cosmetic use, such as skin protection and sunscreen formulations for everyday cosmetics a compound of this invention may be incorporated in auxiliary agents, e.g. a cosmetic base, which are conventionally used for such formulations. Where convenient, other conventional UV-A and/or UV-B screening agents may also be added. The combination of UV filters may show a synergistic effect. The preparation of said light screening agents is well known to the skilled artisan in this field. The concentration of UV filters is not critical. For example, the amount of compounds of the present invention and optionally an additional hydrophilic and/or lipophilic UV-A or UV-B screening agent other than the compounds described in this invention maybe in the range of from 0.5 to 12% by weight of the total composition. These additional screening agents are advantageously selected from the compounds listed below without being limited thereto:

Examples of UV B screening agents, i.e. substances having absorption maxima between about 290 and 320 nm, which come into consideration for combination with the compounds of the present invention are for example the following organic and inorganic compounds: acrylates such as 2-ethylhexyl 2-cyano-3,3-diphenylacrylate (octocrylene, PARSOL® 340), ethyl 2-cyano-3,3-diphenylacrylate and the like; camphor derivatives such as 4-methyl benzylidene camphor (PARSOL® 5000), 3-benzylidene camphor, camphor benzalkonium methosulfate, polyacrylamidomethyl benzylidene camphor, sulfobenzylidene camphor, sulfomethyl benzylidene camphor, therephthalidene dicamphor sulfonic acid and the like; cinnamate derivatives such as octyl methoxycinnamate (PARSOL® MCX), ethoxyethyl methoxycinnamate, diethanolamine methoxycinnamate (PARSOL® Hydro), isoamyl methoxycinnamate and the like as well as cinnamic acid derivatives bond to siloxanes; p-aminobenzoic acid derivatives, such as p-aminobenzoic acid, 2-ethylhexyl p-dimethylaminobenzoate, N-oxypropylenated ethyl p-aminobenzoate, glyceryl p-aminobenzoate; benzophenones such as benzophenone-3, benzophenone-4,2,2', 4,4'-tetra-hydroxy-benzophenone, 2,2'-dihydroxy-4,4'-dimethoxybenzophenone and the like; esters of benzalmalonic acid such as di(2-ethylhexyl)4-methoxybenzalmalonate; esters of 2-(4-ethoxy anilinomethylene)propanedioic acid such as 2-(4-ethoxy anilinomethylene)propanedioic acid diethyl ester as described in EP 895,776; organosiloxane compounds containing benzmalonate groups as described in EP 358,584, EP 538,431 and EP 709,080; drometrizole trisiloxane (MEXORYL XL); pigments such as microparticulated $TiO_2$, and the like, wherein the term "microparticulated" refers to a particle size from about 5 nm to about 200 nm, particularly from about 15 nm to about 100 nm, and which $TiO_2$ particles may be coated by metal oxides such as e.g. aluminum or zirconium oxides or by organic coatings such as e.g. polyols, methicone, aluminum stearate, alkyl silane; imidazole derivatives such as e.g. 2-phenyl benzimidazole sulfonic acid and its salts (PARSOL®HS). Salts of 2-phenyl benzimidazole sulfonic acid are e.g. alkali salts such as sodium- or potassium salts, ammonium salts, morpholine salts, salts of primary, sec. and tert.amines like monoethanolamine salts, diethanolamine salts and the like; salicylate derivatives such as isopropylbenzyl salicylate, benzyl salicylate, butyl salicylate, octyl salicylate (NEO HELIOPAN OS), isooctyl salicylate or homomenthyl salicylate (homosalate, HELIOPAN) and the like; triazine derivatives such as octyl triazone (UVINULT-150), dioctyl butamido triazone (UVASORB HEB), bis ethoxyphenol methoxcyphenyl triazine (TINOSORB S) and the like; a polysiloxane containing a UV-B chromophor like e.g. Polysilicone 15 (Dimethicodiethylbenzalmalonate or Parsol SLX).

Examples of UV A screening agents i.e. substances having absorption maxima between about 320 and 400 nm, which come into consideration for combination with the compounds of the present invention are for example the following organic and inorganic compounds: dibenzoylmethane derivatives such as 4-tert.butyl-4'-methoxydibenzoylmethane (PARSOL® 1789), dimethoxydibenzoylmethane, isopropyldibenzoylmethane and the like; benzotriazole derivatives such as 2,2'-methylene-bis-(6-(2H-benzotriazole-2-yl)-4-(1,1,3,3,-tetramethylbutyl)-phenol (TINOSORB M) and the like; phenylene-1,4-bis-benzimidazolsulfonic acids or salts such as 2,2-(1,4-phenylene) bis-(1H-benzimidazol-4,6-disulfonic acid) (NEOHELIOPAN AP); amino substituted hydroxybenzophenones such as 2-(4-diethylamino-2-hydroxy-benzoyl)-benzoic acid hexylester as described in EP 1,046,391; pigments such as microparticulated ZnO and the like, wherein the term "microparticulated" refers to a particle size from about 5 nm to about 200 nm, particularly from about 15 nm to about 100 nm, and which ZnO particles may be coated by metal oxides such as e.g. aluminum or zirconium oxides or by organic coatings such as e.g. polyols, methicone, aluminum stearate, alkyl silane.

As dibenzoylmethane derivatives have limited photostability it may be desirable to photostabilize these UV-A screening agents. Thus, the term "conventional UV-A screening agent" also refers to dibenzoylmethane derivatives such as e.g. PARSOL® 1789 stabilized by, e.g., 3,3-diphenylacrylate derivatives as described in EP 514,491 and EP 780,119; benzylidene camphor derivatives as described in U.S. Pat. No. 5,605,680; organosiloxanes containing benzmalonate groups as described in EP 358,584, EP 538, 431 and EP 709,080.

The compositions of the invention may also contain usual cosmetic adjuvants and additives, such as preservatives/antioxidants, fatty substances/oils, water, organic solvents, silicones, thickeners, softeners, emulsifiers, additional sunscreens, antifoaming agents, moisturizers, fragrances, surfactants, fillers, sequestering agents, anionic, cationic, nonionic or amphoteric polymers or mixtures thereof, propellants, acidifying or basifying agents, dyes, colorants, pigments or nanopigments, in particular those suited for providing an additional photoprotective effect by physically blocking out ultraviolet radiation, or any other ingredients usually formulated into cosmetics, in particular for the production of sunscreen/antisun compositions. The necessary amounts of the cosmetic and dermatological adjuvants and additives may, based on the desired product, easily be chosen by a skilled artisan in this field and will be illustrated in the examples, without being limited hereto.

An additional amount of antioxidants/preservatives is generally preferred. All known antioxidants usually formulated into cosmetics may be used. Especially preferred are antioxidants chosen from the group consisting of amino acids (e.g. glycine, histidine, tyrosine, tryptophane) and their derivatives, imidazole (e.g urocanic acid) and derivatives, peptides such as D,L-carnosine, D-carnosine, L-carnosine and derivatives (e.g. anserine), carotinoids, carotenes (e.g. α-carotene, β-carotene, lycopene) and derivatives, chlorogenic acid and derivatives, liponic acid and derivatives (e.g. dihydroliponic acid), aurothioglucose, propylthiouracil and other thiols (e.g. thioredoxine, glutathione, cysteine, cystine, cystamine and its glycosyl-, N-acetyl-, methyl-, ethyl-, propyl-, amyl-, butyl- and lauryl-, palmitoyl-; oleyl-, γ-linoleyl-, cholesteryl- and glycerylester) and the salts thereof, dilaurylthiodipropionate, distearylthiodipropionate, thiodipropionic acid and its derivatives (ester, ether, peptides, lipids, nucleotides, nucleosides and salts) as well as sulfoximine compounds (such as buthionine sulfoximine, homocysteine sulfoximine, buthionine sulfone, penta-, hexa-, heptathionine sulfoximine) in very low compatible doses (e.g. pmol/kg to μmol/kg), additionally (metal)-chelators (such as γ-hydroxyfatty acids, palmic-, phytinic acid, lactoferrin), α-hydroxyacids (such as citric acid, lactic acid, malic acid), huminic acid, gallic acid, gallic extracts, bilirubin, biliverdin, EDTA, EGTA and its derivatives, unsaturated fatty acids and their derivatives (such as γ-linoleic acid, linolic acid, oleic acid), folic acid and its derivatives, ubiquinone and ubiquinol and their derivatives, vitamine C and derivatives (such as ascorbyl palmitate and ascorbyl tetraisopalmitate, Mg-ascorbyl phosphate, Na-ascorbyl phosphate, ascorbyl acetate), tocopherol and derivates (such as vitamin-E-acetate, nat. vitamin E and mixtures thereof), vitamin A and derivatives (vitamin A palmitate and acetate) as well as coniferylbenzoat, rutinic acid and derivatives, α-glycosylrutin, ferulic acid, furfurylidene glucitol, butyl hydroxytoluene, butyl hydroxyanisole, trihydroxybutyrophenone, urea and its derivatives, mannose and derivatives, zinc and derivatives (e.g. ZnO, $ZnSO_4$), selenium and derivatives, (e.g. selenomethionine) stilbenes and derivatives (such as stilbenoxide, transstilbenoxide) and suitable derivatives (salts, esters, ethers, sugars, nucleotides, nucleosides, peptides and lipids) of the named active ingredients. One or more preservatives/antioxidants may be present in an amount of about 0.01 wt. % to about 10 wt. % of the total weight of the composition of the present invention. Preferably, one or more preservatives/antioxidants are present in an amount of about 0.1 wt. % to about 1 wt. %.

Examples of emulsifiers that may be used in the present invention in order to form O/W, W/O, O/W/O or W/O/W emulsions/microemulsions include sorbitan oleate, sorbitan sesquioleate, sorbitan isostearate, sorbitan trioleate, polyglyceryl-3-diisostearate, polyglycerol esters of oleic/isostearic acid, polyglyceryl-6 hexaricinolate, polyglyceryl-4-oleate, polygylceryl-4 oleate/PEG-8 propylene glycol cocoate, oleamide DEA, TEA myristate, TEA stearate, magnesium stearate, sodium stearate, potassium laurate, potassium ricinoleate, sodium cocoate, sodium tallowate, potassium castorate, sodium oleate, and mixtures thereof. Further suitable emulsifiers are phosphate esters and the salts thereof such as cetyl phosphate (Amphisol® A), diethanolamine cetyl phosphate (Amphisol®), potassium cetyl phosphate (Amphisol® K), sodium glyceryl oleate phosphate, hydrogenated vegetable glycerides phosphate and mixtures thereof. Furthermore, one or more synthetic polymers may be used as an emulsifier. For example, PVP eicosene copolymer, acrylates/$C_{10-30}$-alkyl acrylate crosspolymer, acrylates/steareth-20 methacrylate copolymer, PEG-22/dodecyl glycol copolymer, PEG-45/dodecyl glycol copolymer, and mixtures thereof. The preferred emulsifiers are cetyl phosphate (Amphisol® A), diethanolamine cetyl phosphate (Amphisol®), potassium cetyl phosphate (Amphisol® K), PVP eicosene copolymer, acrylates/$C_{10-30}$alkyl acrylate crosspolymer, PEG-20 sorbitan isostearate, sorbitan isostearate, and mixtures thereof. Emulsifiers are present in a total amount of about 0.01 wt. % to about 20 wt. % of the total weight of the composition of the present invention. Preferably, about 0.1 wt. % to about 10 wt. % of emulsifier are used.

The lipid phase may advantageously be chosen from: mineral oils and mineral waxes; oils such as triglycerides of caprinic acid or caprylic acid, preferably castor oil; oils or waxes and other natural or synthetic oils, in a preferred embodiment esters of fatty acids with alcohols e.g. isopropanol, propyleneglycol, glycerin or esters of fatty alcohols with lower carboxylic acids or fatty acids; alkylbenzoates; silicone oils such as dimethylpolysiloxane, diethylpolysiloxane, diphenylpolysiloxane, cyclomethicone and mixtures thereof.

Exemplary fatty substances which may be incorporated into the oil phase of the emulsion, microemulsion, oleo gel, hydrodispersion or lipodispersion of the present invention are advantageously chosen from esters of saturated and/or unsaturated, linear or branched alkyl carboxylic acids with 3 to 30 carbon atoms, and saturated and/or unsaturated, linear and/or branched alcohols with 3 to 30 carbon atoms as well as esters of aromatic carboxylic acids and of saturated and/or unsaturated, linear or branched alcohols of 3-30 carbon atoms. Such esters may advantageously be selected from octylpalmitate, octylcocoate, octylisostearate, octyldodeceylmyristate, cetearylisononanoate, isopropylmyristate, isopropylpalmitate, isopropylstearate, isopropyloleate, n-butylstearate, n-hexyllaureate, n-decyloleat, isooctylstearate, isononylstearate, isononylisononanoate, 2-ethyl hexylpalmitate, 2-ethylhexyllaurate, 2-hexyldecylstearate, 2-octyidodecylpalmitate, stearylheptanoate, oleyloleate, oleylerucate, erucyloleate, erucylerucate, tridecylstearate, tridecyltrimellitate, and synthetic, half-synthetic or natural mixtures of such esters e.g. jojoba oil.

Other fatty components suitable for use in the formulation of the present invention include polar oils such as lecithines and fatty acid triglycerides, namely triglycerinic esters of saturated and/or unsaturated, straight or branched carbonic acid with 8 to 24 carbon atoms, preferably of 12 to 18 carbon-atoms whereas the fatty acid triglycerides are preferably chosen from synthetic, half synthetic or natural oils (e.g. cocoglyceride, olive oil, sun flower oil, soybean oil, peanut oil, rape seed oil, sweet almond oil, palm oil, coconut oil, castor oil, hydrogenated castor oil, wheat oil, grape seed oil, macadamia nut oil and others); apolar oils such as linear and/or branched hydrocarbons and waxes e.g. mineral oils, vaseline (petrolatum); paraffins, squalan and squalen, polyolefines, hydrogenated polyisobutenes and isohexadecanes, favored polyolefines are polydecenes; dialkyl ethers such as dicaprylylether; linear or cyclic silicone oils such as preferably cyclomethicone (octamethylcyclotetrasiloxane), cetyldimethicone, hexamethylcyclotrisiloxane, polydimethylsiloxane, poly(methylphenylsiloxane) and mixtures thereof.

Still other fatty components which may advantageously be incorporated into formulations of the present invention include isoeikosane; neopentylglycol diheptanoate; propyleneglycol dicaprylate/dicaprate; caprylic/capric/diglycerylsuccinate; butyleneglycol caprylate/caprate; $C_{12-15}$-alkyllactates; di-$C_{12-15}$-alkyltartrates; triisostearin; dipentaerythrityl hexacaprylate/hexacaprate; propyleneglycol monoisostearate; tricaprylin; dimethylisosorbid. Especially beneficial is the use of mixtures of $C_{12-15}$-alkylbenzoates and 2-ethylhexylisostearate, mixtures of $C_{12-15}$-alkylbenzoates and isotridecylisononanoate as well as mixtures of $C_{12-15}$-alkylbenzoates, 2-ethylhexylisostearate and isotridecylisononanoate.

The oily phase of the formulation of the present invention may also contain natural vegetable or animal waxes such as bee wax, china wax, bumblebee wax and other waxes of insects as well as shea butter and cocoa butter.

A moisturizing agent may be incorporated into a composition of the present invention to maintain hydration or rehydrate the skin. Moisturizers that prevent water from evaporating from the skin by providing a protective coating are called emollients: Additionally an emollient provides a softening or soothing effect on the skin surface and is generally considered safe for topical use. Preferred emollients include mineral oils, lanolin, petrolatum, capric, caprylic triglyceraldehydes, cholesterol, silicones such as dimethicone, cyclomethicone, almond oil, jojoba oil, avocado oil, castor oil, sesame oil sunflower oil, coconut oil and grape seed oil, cocoa butter, olive oil aloe extracts, fatty acids such as oleic and stearic, fatty alcohols such as cetyl and hexadecylalcohol, diisopropyl adipate, hydroxybenzoate esters, benzoic acid esters of $C_{9-15}$-alcohols, isononyl iso-nonanoate, ethers such as polyoxypropylene butyl ethers and polyoxypropylene cetyl ethers, and $C_{12-15}$-alkyl benzoates, and mixtures thereof. The most preferred emollients are hydroxybenzoate esters, aloe vera, $C_{12-15}$-alkyl benzoates, and mixtures thereof. An emollient may be present in an amount of about 1 wt. % to about 20 wt. % of the total weight of the composition. The preferred amount of emollient may be about 2 wt. % to about 15 wt. %, and most preferably about 4 wt. % to about 10 wt. %.

Moisturizers that bind water, thereby retaining it on the skin surface are called humectants. Suitable humectants may be incorporated into a composition of the present invention such as glycerin, polypropylene glycol, polyethylene glycol, lactic acid, pyrrolidon carboxylic acid, urea, phopholipids, collagen, elastin, ceramides, lecithin sorbitol, PEG-4, and mixtures thereof. Additional suitable moisturizers are polymeric moisturizers of the family of water soluble and/or swellable/and/or with water gelating polysaccarides such as hyaluronic acid, chitosan and/or a fucose rich polysaccharide which is e.g. available as Fucogel®1000 (CAS-Nr. 178463-23-5) by SOLABIA S. One or more humectants are optionally present at about 0.5 wt. % to about 8 wt. % in a composition of the present invention, preferably about 1 wt. % to about 5 wt. %.

The aqueous phase of the compositions of the present invention may contain usual cosmetic additives such as alcohols, especially lower alcohols, preferably ethanol and/or isopropanol, low diols oder polyols and their ethers, preferably propylenglycols, glycerin, ethyleneglycol, ethyleneglycol monoethyl- or monobutyl-ether, propylene glycol-monomethyl-, monoethyl- or monobutyl ether, diethylene glycol-monomethyl-or monoethyl-ether and analogue products, polymers, foam stabilisators; electrolytes and especially one or more thickeners. Thickeners that may be used in formulations of the present invention to assist in making the consistency of a product suitable include carbomer, siliciumdioxide, magnesium and/or aluminum silicates, beewax, stearic acid, stearyl alcohol polysaccharides and their derivatives such as xanthan gum, hydroxypropyl cellulose, polyacrylamides, acrylate crosspolymers preferably a carbopole, such as carbopole of type 980, 981, 1382, 2984, 5984 alone or mixtures thereof. Suitable neutralizing agents which may be included in the composition of the present invention to neutralize components such as e.g. an emulsifier or a foam builder/stabilizer include but are not limited to alkali hydroxides such as a sodium and potassium hydroxide; organic bases such as diethanolamine (DEA), triethanolamine (TEA), aminomethyl propanol, and mixtures thereof; amino acids such as arginine and lysine and any combination of any foregoing. The neutralizing agent may be present in an amount of about 0.01 wt. % to about 8 wt. % in the composition of the present invention, preferably, 1 wt. % to about 5 wt. %.

The addition of electrolytes into the composition of the present invention may be necessary to change the behavior of a hydrophobic emulsifier. Thus the emulsions/microemulsions of this invention may preferably contain electrolytes of one or several salts including anions such as a chloride, a sulfate, a carbonate, a borate or an aluminate, without being limited thereto. Other suitable electrolytes may be on the bases of organic anions such as, but not limited to, lactate, acetate, benzoate, propionate, tartrate and citrate. As cations preferably ammonia, alkylammonia, alkali- or alkaline earth metals, magnesium-, iron- or zinc-ions are selected. Especially preferred salts are potassium and sodium chloride, magnesium sulfate, zinc sulfate and mixtures thereof. Electrolytes are present in an amount of about 0.01 wt. % to about 8 wt. % in the composition of the present invention.

The cosmetic compositions of the invention are useful as compositions for photoprotecting the human epidermis or hair against the damaging effect of ultraviolet irradiation, as antisun/sunscreen composition or as makeup product. Such compositions can, in particular, be provided in the form of a lotion, a thickened lotion, a gel, a cream, a milk, an ointment, a powder or a solid tube stick and may optionally be packaged as an aerosol and may be provided in the form of a mousse, foam or a spray. When the cosmetic composition according to the invention is provided for protecting the human epidermis against UV radiation or as antisun/sunscreen composition, it may be in the form of a suspension or dispersion in solvents or fatty substances, or alternatively in the form of an emulsion or microemulsion (in particular of O/W or W/O type, O/W/O or W/O/W-type), such as a cream or a milk, a vesicular dispersion, in the form of an ointment, a gel, a solid tube stick or an aerosol mousse. The emulsions can also contain anionic, nonionic, cationic or amphoteric surfactants.

When the cosmetic composition according to the invention is used for protecting the hair, it may be in the form of a shampoo, a lotion, a gel or a rinse out composition, to be applied before or after shampooing, before or after dyeing or bleaching, before, during or after permanent-waving or hair straightening operation, a styling or treatment lotion or a gel, a blow-drying or hairsetting lotion or gel, a hair lacquer, or a composition for permanent-waving, straightening, dyeing or bleaching the hair.

When the cosmetic composition according to the invention is used as makeup product for eyelashes, the eyebrows, the skin or the hair, such as an epidermal treatment cream, a foundation, a tube of lipstick, an eyeshadow, a face powder, an eyeliner, a mascara or a coloring gel, it may be solid or pasty, anhydrous or in aqueous form, such as O/W or W/O emulsion, suspension or gel.

The present invention also features formulating the organosilicone compounds according to the invention as an agent for screening out UV radiation, in particular for controlling the color of human skin.

The organosilicone compounds according to this invention show an excellent liposolubility and can thus be incorporated in high concentrations into cosmetic formulations which leads to high protection factor of the final compositions. Additionally they are homogeneously distributed in the cosmetic formulation containing at least a fatty phase and an cosmetically accepted organic solvent which leads, applied on the skin/or hair, to the formation of a protective film which protects effectively the skin and/or hair against the deleterious effects of UV-radiation.

Thus, it is another object of the present invention to use the compounds of the invention for protecting the skin and/or hair against ultraviolet radiation, in particular solar radiation, comprising topically applying an effective amount of a cosmetic composition containing the organosilicone compounds according to the invention.

Finally, this invention also features non-therapeutic regime/regimen for controlling the variation of the color of the skin caused by ultraviolet radiation, comprising topically applying onto the skin an effective amount of a cosmetic composition containing organosilicone compounds according to the invention.

According to another embodiment of the invention, a organosilicone compound of this invention can be used as protecting agent against UV radiation for plastics.

The organosilicone derivatives of the invention are also photostable.

In accordance with the foregoing the invention provides
(1) An organosilicone compound for use as a UVA filter, e.g. for use in a cosmetic composition;
(2) A cosmetic composition comprising an organosilicone compound as under (1) as active ingredient together with cosmetically accepted adjuvants and additives, in particular a composition further comprising a screening agent selected from the group consisting of UV-A screening agents, UV-B screening agents, and mixtures thereof, e.g. a complementary anorganic UV screening agent, such as a coated or uncoated pigment or nanopigment of a metaloxide selected from the oxides of titanium, zinc, iron, zirconium and cerium;
(3) A cosmetic composition comprising an organosilicone compound as under (1) as active ingredient together with cosmetically accepted adjuvants and additives for protecting human hair and/or skin against damage in which UVA irradiation plays a role or is implicated;
(4) A method to the protection of human hair and/or skin against damage in which UVA irradiation plays a role or is implicated which comprises topically applying an effective amount of an organosilicone compound as under (1);
(5) Use of an organosilicone compound as under (1) for protecting human hair and/or skin against damage in which UVA irradiation plays a role or is implicated.

The following examples are provided to further illustrate the processes and compositions of the present invention. These examples are illustrative only and are not intended to limit the scope of the invention in any way. In the Examples, FC. means Flash chromatography; HV means high vacuum (0.1 Pa or below); INCI means International Nomenclature Cosmetic Ingredients. All structures were unambiguously identified via $^1$H-NMR (300 MHZ, CDCl$_3$). The photostability of the products were measured according to Berset et. al.; Internat. J. Cosmetic Science 18:167-177 (1996).

EXAMPLE A1

Preparation of
2-(4-diethylamino-2-hydroxybenzoyl)benzoic acid
prop-2-ynyl ester A mixture of 32 mmol 2-(4-diethylamino-2-hydroxybenzoyl)benzoic acid, 160 mmol propargylic alcohol and 32 mmol H$_2$SO$_4$ is refluxed for 48 h. After evaporation of the excess propargylic alcohol the residue is dissolved in ethylacetate and subsequently washed twice with saturated NaHCO$_3$ solution and twice with water. After drying (Na$_2$SO$_4$), the solvent is evaporated (HV) and the crude product purified twice via FC (n-hexane/EtOAC 1:1, hexane/MTBE 4/1-1/1) yielding 2-(4-diethylamino-2-hydroxybenzoyl)benzoic acid prop-2-ynyl ester. MS (EI): 374 (18%, M+Na$^+$), 352 (100%, M+H$^+$), 296 (17%). UV (EtOH): $\lambda_{max}$=356 nm ($\epsilon$=31'648).

EXAMPLE A2

Preparation of
2-(4-diethylamino-2-hydroxybenzoyl)benzoic acid
allyl ester

A mixture of 32 mmol 2-(4-diethylamino-2-hydroxybenzoyl)benzoic acid, 160 mmol allylic alcohol and 32 mmol H$_2$SO$_4$ is refluxed for 48 h. After evaporation of the excess allylic alcohol the residue is dissolved in ethyl acetate and subsequently washed twice with saturated NaHCO$_3$ solution and twice with water. After drying (Na$_2$SO$_4$), the solvent is evaporated (HV) and the crude product purified via FC (n-hexane/EtOAC 2:1, hexane) yielding 2-(4-diethylamino-2-hydroxybenzoyl)benzoic acid allyl ester. MS (EI): 376 (10%, M+Na$^+$), 354 (100%, M+H$^+$), 296 (17%). UV (EtOH): $\lambda_{max}$=354 nm ($\epsilon$=34'257).

EXAMPLE A3

Preparation of
2-(4-diethylamino-2-hydroxybenzoyl)-propargylic
benzamide

A mixture of 6 g of 2-(4-diethylamino-2-hydroxybenzoyl) benzoic acid and 1.6 g of propargylic amine is dissolved in 20 ml of DMF with cooling to form a clear solution. 5.9 g of dicyclohexylcarbodiimide is slowly added to this solution. The mixture is diluted with 20 ml of CH$_2$Cl$_2$ and left at room temperature for two hours. The suspension formed is filtered and washed with hexane and ether. The organic phase is diluted with EtOAc, washed with saturated NaHCO$_3$ solution, three times with water and once with saturated NaCl solution. After drying (Na$_2$SO$_4$), the solvent is evaporated (HV) and the crude product purified via FC (n-hexane/EtOAC 2:1, hexane) and recrystallized from a mixture of hexane, toluene and EtOAc, yielding white crystals of 2-(4-diethylamino-2-hydroxybenzoyl)-propargylic benzamide. MS: 351 (M+H$^+$), 333, 296 (100%).

EXAMPLE B1

Preparation of a COMPOUND wherein B, B', R$^1$,
R$^6$, R$^7$, R$^8$, R$^9$, R$^{10}$ and R$^{11}$ are methyl, Z is a
Group of Formula III wherein R$^3$ and R$^4$ are ethyl
and —X—Y— is —O—CH$_2$—C(CH$_2$)— (major
isomer), r is in its Statistical Mean 14 and s is in
its Statistical Mean 4

A solution of 1.75 mmol of 2-(4-diethylamino-2-hydroxybenzoyl)benzoic acid prop-2-ynyl ester and 1.75 mmol eq. SiH of a COMPOUND wherein B, B', R$^1$ and R$^2$ are methyl, Z is H, r is in its statistical mean 14 and s is in its statistical mean 4 (MW~1500) in 3 ml toluene under an inert atmosphere is heated to 55° C. A catalytic amount of platinum carbon 5% is added and the reaction is kept at 55° C. for 20 h. The product solution is washed with a mixture of water/methanol=1:10, dried (Na$_2$SO$_4$), and concentrated. After the residue is dissolved in 3 ml toluene, active charcoal is added and the mixture is stirred for 2 d at RT. After filtration over Celite the solvent is evaporated to yield a yellow oil (two isomers). UV (EtOH): 354 nm (E=477), having unlimited solubility in Cétiol LC and Crodamol DA and excellent photostability qualities in film.

EXAMPLE B2

Preparation of a COMPOUND wherein B, B', $R^1$, $R^6$, $R^7$, $R^8$, $R^9$, $R^{10}$ and $R^{11}$ are methyl, Z is a Group of Formula III wherein $R^3$ and $R^4$ are ethyl and —X—Y— is —O—$CH_2$—C($CH_2$)— (Major Isomer), r is in its Statistical Mean 60 and s is in its Statistical Mean 4

0.5 g of 2-(4-diethylamino-2-hydroxybenzoyl)benzoic acid prop-2-ynyl ester, 2 g of polysiloxane AE-151 of Wacker-Chemie GmbH, and a catalytic amount of platinum carbon 5% in 10 ml of xylene are placed in a three-necked reaction flask under an inert atmosphere and heated for 2 h at 70° C. The product solution is filtered through Celite, washed with a mixture of water/methanol=1:10 and concentrated to yield a brownish oil (two isomers). UV 354 nm (E=147), having unlimited solubility in Cétiol LC and Crodamol DA and excellent photostability qualities in film.

EXAMPLE B3

Preparation of a COMPOUND wherein B, B', $R^1$, $R^6$, $R^7$, $R^8$, $R^9$, $R^{10}$ and $R^{11}$ are methyl, Z is a Group of Formula III wherein $R^3$ and $R^4$ are ethyl and —X—Y— is —NH—$CH_2$—C($CH_2$)— (Major Isomer), r is 0 and s is 1

A solution of 1.4 mmol of 2-(4-diethylamino-2-hydroxybenzoyl)-propargylic benzamide and 1.2 mmol of heptamethyltrisiloxane of formula IV wherein B, B', $R^1$ and $R^2$ are methyl, Z is hydrogen, r is 0 and s is 1, in 10 ml of toluene under an inert atmosphere is heated to 55° C. A catalytic amount of platinum-divinyl-tetramethyl-disiloxane complex is added and the reaction is kept at 80 to 85° C. for 36 hours and at 100° C. for four hours. 0.3 g of additional heptamethyltrisiloxane and a small amount of catalyst are added. After heating for another 18 hours at reflux, the product solution is concentrated and chromatographed twice ($CH_2Cl_2$/MeOH) to yield the product (two isomers). UV (EtOH): 358 nm (E=227).

EXAMPLE C1

Preparation of a Broad Spectrum Sunscreen Lotion Containing 2% of a Organosilicone Compound of the Invention

| Part | wt % | compound | INCI name |
|---|---|---|---|
| A | 2.00 | PARSOL MCX | octyl methoxycinnamate |
|  | 2.00 | organosilicone compound of the invention |  |
|  | 3.00 | PARSOL 1789 | 4-tert. butyl-4'-methoxy-dibenzoyl-methane |
|  | 12.00 | CETIOL LC | coco-caprylate/caprate |
|  | 4.00 | DERMOL185 | isostearyl neopentanoate |
|  | 0.25 | diethyleneglycolmonostearate | PEG-2-stearate |
|  | 1.00 | cetylalcohol | cetylalcohol |
|  | 0.25 | MPOB/PPOB | methyl-propylparabene |
|  | 0.10 | EDTA BD | EDTA-disodium salt |
|  | 1.00 | AMPHISOL DEA | diethanolamine cetylphosphate |
| B | 20.00 | PERMULENE TR-1 (+%) | Acrylate C10-C30 Alkylacrylate |
|  | 48.60 | deionized water | deionized water |
|  | 5.00 | propyleneglycol | 1,2-propanediol |
|  | 0.80 | KOH (10%) | potassium hydroxide |

Part A is heated in a reactor to 85° C. Part B is slowly added within 10 minutes, followed by addition of KOH, cooling and degassing of the emulsion.

EXAMPLE C2

Preparation of a Broad Spectrum Sunscreen Lotion Containing 4% of a Organosilicone Compound of the Invention

| Part | wt % | compound | INCI name |
|---|---|---|---|
| A | 3.00 | PARSOL MCX | octyl methoxycinnamate |
|  | 4.00 | organosilicone compound of the invention |  |
|  | 3.00 | PARSOL 500 | 4-methylbenzylidene camphor |
|  | 4.00 | PARSOL 1789 | 4-tert. butyl-4'-methoxy-dibenzoyl-methane |
|  | 2.00 | glyceryl monostearate | glyceryl stearate |
|  | 2.00 | cetylalcohol extra | cetylalcohol |
|  | 2.00 | GANEX V-220 | PVP/eicosene copolymer |
|  | 4.00 | CERAPHYL 375 | isostearyl neopentanoate |
|  | 4.00 | CERAPHYL 847 | octyldodecyl stearoyl stearate |
|  | 2.00 | AMPHISOL K | potassium cetylphosphate |
|  | 0.10 | EDTA BD | EDTA-disodium salt |
|  | 0.60 | PHENONIP | phenoxyethanol & methyl, ethyl, propyl & butyl paraben |
| B | 11.15 | deionized water | deionized water |
|  | 50.00 | CARBOPOL 934 (1% solution) | carbomer |
|  | 5.00 | propyleneglycol | 1,2-propanediol |
|  | 0.15 | NIPAGIN M | methylparaben |
|  | 3.00 | KOH (10%) | potassium hydroxide |
|  | q.s. | perfume oil | fragrance |

Part A is heated in a reactor to 85° C. The homogeneous Part B is added followed by addition of preheated KOH (75° C.), cooling and degassing of the emulsion.

EXAMPLE C3

Preparation of a Broad Spectrum Sunscreen Cream Containing 4% of a Polysiloxane Compound of the Invention

| Part | wt % | compound | INCI name |
|---|---|---|---|
| A | 8.00 | PARSOL SLX | dimethico-diethylbenzalmalonate |
|  | 4.00 | organosilicone compound of the invention |  |
|  | 6.00 | T-COTE 031 | titanium dioxide & dimethicone |
|  | 10.00 | ESTOL GTEH 3609 | trioctanoin |
|  | 1.00 | cetyl alcohol | cetyl alcohol |

-continued

| Part | wt % | compound | INCI name |
|---|---|---|---|
| | 4.00 | ESTOL GMM 3650 | glyceryl myristate |
| | 0.05 | butylated hydroxytoluene | BHT |
| | 0.10 | EDTA BD | disodium EDTA |
| | 0.60 | PHENONIP | phenoxyethanol & methyl-, ethyl-propyl- & butyl-paraben |
| | 2.00 | AMPHISOL K | potassium cetyl phosphate |
| B | 50.75 | deionized water | deionized water |
| | 10.00 | CARBOPOL 980 1% solution | Carbomer 980 |
| | 3.00 | glycerin | glycerin |
| C | 0.50 | KOH 10% solution | potassium hydroxide |
| | q.s | perfume oil | fragrance |

Part A is heated to 85° C. while stirring and then mixed for 30 seconds with a turbine at 8000 t/minutes. When homogeneous, Part B is pre-heated to 75° C. and added to Part A. The mixture is cooled to 40° C. and Part C is added. The water loss is compensated and stirring is continued while cooling to ambient temperature. Then the mixture is mixed for 30 seconds with a turbine at 8000 t/minute.

The cream has a low skin penetration quality.

What is claimed is:

1. An organosilicone compound comprising a unit of formula I $$Z-Si R^1_a-O_{(3-a)/2} \quad (I)$$

wherein
a is 0, 1 or 2,
$R^1$ is hydrogen, a saturated or unsaturated $C_1$-$C_{30}$hydrocarbon group or a trimethylsilyloxy group; and
Z is an amino substituted hydroxybenzophenone of formula III (III)

wherein
$R^3$ and $R^4$ independently are hydrogen, $C_1$-$C_{20}$alkyl, $C_2$-$C_{20}$alkenyl, $C_3$-$C_{10}$cycloalkyl or $C_3$-$C_{10}$cycloalkenyl or $R^3$ and $R^4$, together with the nitrogen atom they are bound to, form a 5 to 6 membered ring;
X is —O— or —NR$^5$- wherein $R^5$ is hydrogen, $C_1$-$C_{20}$alkyl, $C_2$-$C_{20}$alkenyl, $C_3$-$C_{10}$cycloalkyl or $C_3$-$C_{10}$cycloalkenyl; and
Y is a divalent $C_3$-$C_{12}$alkylene or alkenylene chain;
and, optionally, a unit of formula II $$Si R^2_b-O_{(4-b)/2} \quad (II)$$

wherein
b is 0, 1, 2, 3; and
$R^2$ is hydrogen, a saturated or unsaturated $C_1$-$C_{30}$hydrocarbon group or a trimethylsilyloxy group.

2. An orpanosilicone compound according to claim 1 which is a linear diorgano-siloxane polymer comprising one structural unit of formula IVa and one structural unit of formula IVb $$B-Si R^6 R^7- \quad (IVa)$$

$$-O-Si R^8 R^9-B' \quad (IVb)$$

s units of formula IVc $$-O-Si R^1 Z- \quad (IVc)$$

and r units of formula IVd $$-O-Si R^{10} R^{11}- \quad (IVd)$$

wherein
Z is as defined in claim 1;
$R^1$, $R^6$, $R^7$, $R^8$, $R^9$, $R^{10}$ and $R^{11}$ independently are as defined in claim 1 for $R^2$ ;
B and B' independently are a group Z or a group $R^2$;
r is an integer from 0 to 200; and
s is an integer from 0 to 50, wherein at least B or B is Z when s is 0.

3. A process for the preparation of an organosilicone compound according to claim 1 comprising reacting (hydrosilylating) an organosilicone compound comprising a unit of formula VI $$H-Si R^1_a-O_{(3-a)/2} \quad (VI)$$

wherein
a is 0, 1 or 2; and
R¹ is hydrogen, a saturated or unsaturated C$_1$-C$_{30}$hydrocarbon group or a trimethylsilyloxy group; and, optionally, a unit of formula II according to claim 1, with a compound of formula VII

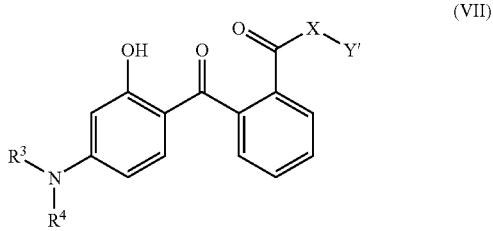

(VII)

in which R³, R⁴ X are as defined in claim 1 and Y' has the same definition as Y in claim 1, but is terminated either with a double or a triple bond.

4. A cosmetic composition comprising an organosilicone compound as in claim 1 together with cosmetically accepted adjuvants and additives.

5. A cosmetic composition comprising an organosilicone compound as in claim 1 for protecting human hair and/or skin against damage in which UVA irradiation plays a role or is implicated.

6. A method to the protection of human hair and/or skin against damage in which UVA irradiation plays a role or is implicated which comprises topically applying an effective amount of an organosilicone compound as in claim 1.

* * * * *